United States Patent
Bar et al.

(10) Patent No.: US 10,964,435 B2
(45) Date of Patent: Mar. 30, 2021

(54) METHOD OF MONITORING THE BEHAVIOR OF A COHORT GROUP OF MEMBERS

(71) Applicant: ESSILOR INTERNATIONAL (COMPAGNIE GENERALE D'OPTIQUE), Charenton-le-Pont (FR)

(72) Inventors: Nathalie Bar, Charenton-le-Pont (FR); Cecile Doussinault, Charenton-le-Pont (FR); Clotilde Haro, Charenton-le-Pont (FR)

(73) Assignee: Essilor International, Charenton-Ie-Pont (FR)

( * ) Notice: Subject to any disclaimer, the term of this patent is extended or adjusted under 35 U.S.C. 154(b) by 855 days.

(21) Appl. No.: 15/494,068

(22) Filed: Apr. 21, 2017

(65) Prior Publication Data
US 2017/0311860 A1    Nov. 2, 2017

(30) Foreign Application Priority Data

Apr. 28, 2016 (EP) ..................................... 16305497

(51) Int. Cl.

| | |
|---|---|
| *G16H 50/70* | (2018.01) |
| *A61B 3/02* | (2006.01) |
| *H04W 4/08* | (2009.01) |
| *H04H 60/33* | (2008.01) |
| *A61B 5/16* | (2006.01) |
| *G16H 40/67* | (2018.01) |
| *H04L 29/08* | (2006.01) |

(52) U.S. Cl.
CPC ............... *G16H 50/70* (2018.01); *A61B 3/02* (2013.01); *A61B 5/16* (2013.01); *G16H 40/67* (2018.01); *H04L 67/306* (2013.01); *H04W 4/08* (2013.01); *H04H 60/33* (2013.01)

(58) Field of Classification Search
CPC ... A61B 5/16; A61B 3/02; H04W 4/08; H04L 67/306; G06F 19/34; H04H 60/33
See application file for complete search history.

(56) References Cited

U.S. PATENT DOCUMENTS

| | | | |
|---|---|---|---|
| 7,199,767 B2 * | 4/2007 | Spero | G02B 5/20 345/7 |
| 8,159,519 B2 * | 4/2012 | Kurtz | H04N 7/147 348/14.01 |
| 10,510,137 B1 * | 12/2019 | Kitain | G02B 27/0093 |

(Continued)

FOREIGN PATENT DOCUMENTS

WO    WO 2015109145    7/2015

OTHER PUBLICATIONS

European Search Report dated Oct. 25, 2016 in corresponding European Patent Application No. 16305497.

*Primary Examiner* — Jacqueline Cheng
*Assistant Examiner* — Tho Q Tran
(74) *Attorney, Agent, or Firm* — Nixon & Vanderhye

(57) ABSTRACT

A method of monitoring the behavior of a cohort group of members, including: a cohort group behavior monitoring step during which the behavior of the members of the cohort group of members is monitored so as to provide behavior data; and a vision information generating step during which vision information relating to the vision of the members of the cohort group is generated based on the monitoring of the behavior data over time.

15 Claims, 2 Drawing Sheets

(56) References Cited

U.S. PATENT DOCUMENTS

| | | | |
|---|---|---|---|
| 2008/0100800 A1* | 5/2008 | Guillen | A61B 3/1015 351/205 |
| 2012/0206268 A1 | 8/2012 | Morris | |
| 2012/0239471 A1* | 9/2012 | Grimm | G06Q 30/0265 705/14.5 |
| 2014/0146156 A1 | 5/2014 | Strombom et al. | |

* cited by examiner

METHOD OF MONITORING THE BEHAVIOR OF A COHORT GROUP OF MEMBERS

TECHNICAL FIELD

The invention relates to a method of monitoring the behavior of a cohort group of members so as to generate a vision information relating to the vision of the members of the cohort group, a behavior monitoring device and a controlled environment configured to receive a cohort group of member so as to monitor the behavior of such cohort group.

BACKGROUND OF THE INVENTION

Usually, an eyewear equipment wearer wishing to have an eyewear equipment goes to see an eye care practitioner.

The eye care practitioner may carry out a number of tests to determine the most appropriate eyewearer equipment for the wearer.

The tests carried out by the eye care practitioner are usually in specific conditions and over short periods of times. Furthermore, the tests only cover part of the very different visual situation the wearer may face. Therefore, the eyewear equipment settings correspond to the best average compromise between the different visual situations the wearer may face based on the visual test carried out at a given point in time.

Furthermore, the tests carried out on different persons are carried out in a sequenced manner, making the comparison between different individuals or the determination of a group behavior very difficult.

Since the visual requirements and behavior of a person may change over time or depending on the situation, there is a need for a system and a method for monitoring the behavior of a group of members so as to determine a vision information.

An aim of the present invention is to propose such a system and method for monitoring the behavior of a cohort group of members.

SUMMARY OF THE INVENTION

To this end, the present invention relates to a method of monitoring the behavior of a cohort group of members, for example implemented by computer means, comprising:
  a cohort group behavior monitoring step during which the behavior of the members of the cohort group of members is monitored so as to provide behavior data,
  a vision information generating step during which vision information relating to the vision of the members of the cohort group is generated based on the monitoring of the behavior data over time.

Advantageously, the method of the invention by monitoring behavior of the members of the cohort group of members over time allows generating vision information relating to the vision of the members of the cohort group.

According to further embodiments which can be considered alone or in combination:
  the behavior data are measured data and/or declarative data; and/or
  the behavior data relate to the behavior of the cohort group or of a sub-group of members of the cohort group, for example each member of the cohort group; and/or
  the behavior data relate to postural behavior of the members of the cohort group, and/or to the visual behavior of the members of the cohort group, for example the refraction of each members of the cohort group; and/or
  the method further comprises a stimulus exposing step during which at least part of the members of the cohort group are exposed to a stimulus over a period of time prior and/or during the cohort group behavior monitoring step; and/or
  the method further comprises a cohort group member profile data providing step during which profile data relating to the profile of each member of the cohort group is provided, the profile of each member comprising at least features relating to the vision of each member and/or the behavior of each member, and the profile of each member are taken into account when generating the vision information; and/or
  the stimulus is selected based on the profile data; and/or
  the stimulus is a visual stimulus and/or an auditory stimulus; and/or
  the method further comprises an activity providing step during which an activity to be carried out by at least part of the members of the cohort group is provided and the behavior of the members of the cohort group is monitored while having the members carry out said activity; and/or
  the method further comprises an environment data providing step during which environment data relative to the environment of the cohort group upon monitoring of the behavior is provided, and the environment data are taken into account when generating the vision information; and/or
  the environment data are measured data and/or declarative data and/or retrieved from a database; and/or
  the cohort group behavior data monitoring step is implemented in a controlled environment, for example a controlled visual environment; and/or
  the method further comprises prior to the cohort group behavior monitoring step:
    a behavior monitoring device providing step during which a behavior monitoring device configured for monitoring behavior of a cohort group of members is provided,
    a initialization step during which the behavior monitoring device is initialized based on the profile data and/or the environment data; and/or
  during the vision information generating step the information is generate using statistical analysis of behavior data over time; and/or
  the vision information relates to a recommendation, for example a lens design recommendation and/or an ophthalmic lens recommendation, and/or an alert, for example an alert indicative of the vision state, and/or an activation of at least one functionality on a head mounted device and/or an access to a service offer, and/or a comparison information relating to the comparison of the behavior of the members of the cohort group relative to a behavior reference model of the cohort group, and/or a comparison information relating to the comparison of the behavior of at least one members of the cohort group relative to a behavior reference model of said member of the cohort group; and/or
  the method further comprising a behavior deviation detection step during which a behavior deviation of at least one member of the cohort group relative to the behavior of the other members of the group and/or relative to the model behavior of the at least one member of the cohort group is detected; and/or the method further comprising an enhance behavior data monitoring step during which upon detection of a behavioral deviations in the members of the cohort group, at least one member of the cohort group is identified as a person of interest and is subject to an enhance level of monitoring, for example by monitoring additional features and/or by increasing the monitoring frequency; and/or the method further comprises a segmentation step during which the cohort group is segmented in sub-group of members based at least on the behavior data; and/or the segmentation of the cohort group is further based on the profile of each member; and/or the method further comprises an optical device providing step during which optical devices are provided to at least part of the members of the cohort group and the vision information relates to the performance of the optical devices; and/or the optical devices are ophthalmic devices and/or filtering devices and/or head mounted display devices.

The invention also relates to a behavior monitoring device configured for monitoring behavior of a cohort group of members, the device comprising:
 a communication unit configure to receive behavior data relating to the behavior of the members of a cohort group of members,
 a memory storing computer executable instructions and configured to store the received behavior data;
 a processor for executing the computer executable instructions,
wherein the computer executable instructions comprise instructions for generating vision information relating to the vision of the members of the cohort group based on the monitoring of the behavior data over time.

According to further embodiments which can be considered alone or in combination:

the behavior monitoring device further comprises at least one sensor configured to sense behavior data and to send said behavior data to the communication unit; and/or the communication unit is configured to receive measured and/or declarative behavior data; and/or the communication unit is configured to receive behavior data relating to the behavior of the cohort group or of a sub-group of members of the cohort group, for example each member of the cohort group; and/or the communication unit is configured to receive behavior data relating to postural behavior of the members of the cohort group, and/or to the visual behavior of the members of the cohort group, for example the refraction of each members of the cohort group; and/or the behavior monitoring device further comprise a stimulus unit configured to expose at least part of the member of the cohort group to a stimulus over a period of time prior and/or simultaneous to receiving the behavior data the computer executable instructions comprise instructions for taking into account the stimulus when generating the vision information; and/or the communication unit is configured to receive and the memory is further configured to store cohort group member profile data relating to the profile of each member of the cohort group, the profile of each member comprising at least features relating to the vision of each member and/or the behavior of each member, and the profile of each member are taken into account when generating the vision information; and/or the stimulus unit is configured to select the stimulus based on the profile data; and/or the stimulus unit is configured to generate a visual stimulus and/or an tactile, auditory stimulus; and/or the communication unit is configured to receive and the memory is further configured to store activity data indicative of activity carried out by at least part of the members of the cohort group and the computer executable instructions comprise instructions for taking into account the activity data when generating the vision information; and/or the communication unit is configured to receive and the memory is further configured to store environment data relative to the environment of the cohort group upon monitoring of the behavior, and the computer executable instructions comprise instructions for taking into account the environment data when generating the vision information; and/or the communication unit is configured to receive environment data that are measured data and/or declarative data and/or retrieved from a database; and/or the communication unit is configured to receive and the memory is further configured to store environment data relative to a controlled environment in which the monitoring is carrying out, and the computer executable instructions comprise instructions for taking into account the environment data when generating the vision information; and/or the computer executable instructions comprise instructions for initializing the behavior device based on the profile data and/or the environment data; and/or the computer executable instructions comprise instructions for generating vision information using statistical analysis of behavior data over time; and/or the computer executable instructions comprise instructions for generating a recommendation, for example a lens design recommendation and/or an ophthalmic lens recommendation, and/or an alert, for example an alert indicative of the vision state, and/or an activation of at least one functionality on a head mounted device and/or an access to a service offer, and/or a comparison information relating to the comparison of the behavior of the members of the cohort group relative to a behavior reference model of the cohort group, and/or a comparison information relating to the comparison of the behavior of at least one members of the cohort group relative to a behavior reference model of said member of the cohort group; and/or the computer executable instructions comprise instructions for detecting a behavior deviation at least one member of the cohort group relative to the behavior of the other members of the group and/or relative to the model behavior of the at least one member of the cohort group is detected; and/or the computer executable instructions comprise instructions for enhancing behavior data monitoring upon detection of a behavioral deviations in the members of the cohort group, at least one member of the cohort group is identified as a person of interest and is subject to an enhance level of monitoring, for example by monitoring additional features and/or by increasing the monitoring frequency; and/or the computer executable instructions comprise instructions for segmenting the cohort group is segmented in sub-group of members based at least on the behavior data; and/or the segmentation of the cohort group is further based on the profile of each member; and/or the communication unit is configured to receive and the memory is further configured to store optical device data relative to optical devices are provided to at least part of the members of the cohort group, and the computer executable instructions comprise instructions for taking into account the optical device data when generating the vision information; and/or the optical devices are ophthalmic devices and/or filtering devices and/or head mounted display devices.

The invention further relates to a controlled environment configured to receive a cohort group of members, the controlled environment comprising:

means for controlling at least visual environment of the cohort group, a plurality of sensors configured to measure behavior of the members of the cohort group, a communication unit configured to send the measured behavior data to a behavior monitoring device according to the invention.

According to a further aspect of the invention, the invention relates to a computer program product comprising one or more stored sequences of instructions that are accessible to a processor and which, when executed by the processor, causes the processor to carry out the steps of the method according to the invention.

The invention further relates to a computer readable medium carrying one or more sequences of instructions of the computer program product according to the invention.

Furthermore, the invention relates to a program which makes a computer execute the method of the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

BRIEF DESCRIPTION OF THE DRAWINGS

Other features and advantages of the present invention will become apparent from the following description of non-limitative embodiments, with reference to the attached drawing in which.

Figure 1:
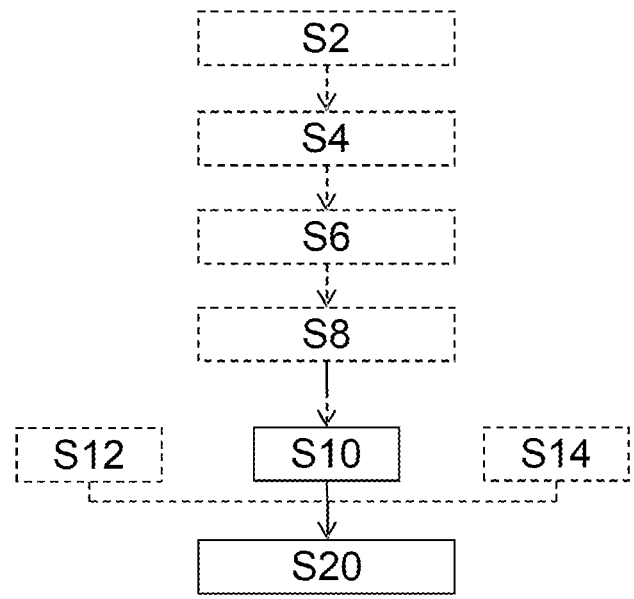
FIG. 1 is an illustration of a chart-flow of a monitoring method according to the invention.

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects.

DETAILED DESCRIPTION OF EMBODIMENTS OF THE INVENTION

The invention relates to a method for generating vision information by monitoring the behavior of a cohort group of members.

As illustrated on FIG. 1, the method of the invention comprises at least:

a cohort group behavior monitoring step S10, and a vision information generating step S20.

During the cohort group behavior monitoring step 10, the behavior of the members of the cohort group of members is monitored so as to provide behavior data.

The behavior data may be measured data. The behavior data may be measured using a mounted sensing device provided to each member of the cohort group. For example, the mounted sensing device may be a head mounted device comprising at least one sensor such as a camera adapted to acquire data relating to the behavior of at least one member of the cohort group. The mounted sensing device may be configured to sense behavior data of the member wearing the sensing device and/or of other members of the cohort group.

The behavior data may be measured using a set of sensing devices, such as cameras, provided in the environment of the cohort group.

For example, the cohort group of members may be placed in a controlled environment comprising a plurality of sensors configured to measure behavior of the members of the cohort group.

The behavior data may be measured using both mounted sensing devices and at least one set of sensing devices provided in the environment of the cohort group.

The behavior data may also be declarative data. For example, each member of the cohort group is requested to fill out a form with questions in relation to his or her own behavior and/or in relation to the behavior of other members of the cohort group, eventually of the cohort group as a whole.

The behavior data may relate to the behavior of the cohort group or of a sub-group of members of the cohort group, for example each member of the cohort group.

The behavior data relate to postural behavior of the members of the cohort group, and/or to the visual behavior of the members of the cohort group, for example the refraction of each members of the cohort group.

The postural behavior may relate to the posture of the whole body or of specific parts of the body, for example the head, eyes, the balance of each member of the cohort group.

The visual behavior may provide indication relating to the gazing behavior of each member, such as gazing direction, gazing distances, variation of gazing distances.

The visual behavior may further relate to oculomotor parameters of each member, such as eye movements, saccades, accommodation, convergence.

The visual behavior may further relate to ocular parameters of each member, such as opening of the eyelid, pupil diameter, blink frequency, duration of the blink, and strength of the blink.

The visual behavior may further relate to the accommodation fluctuation of each member and/or the relative movement of the head and the eyes of each member.

According to an embodiment, the members of the cohort group may wear optical equipments and the visual behavior may further relate to the relative position of the optical equipment and a reference point on each member, for example on the face or head of each member. The visual behavior may further relate to the zone of the optical equipment through which each member looks when using the optical equipment.

During the vision information generating step S20, vision information relating to the vision of the members of the cohort group is generated based on the monitoring of the behavior data over time.

The vision information may relate to a recommendation for at least part of the members of the cohort group.

For example, the recommendation may be a lens design recommendation and/or an ophthalmic mean recommendation and/or an adaptation of the visual behavior. The ophthalmic mean may include contact lenses and/or ophthalmic lenses and/or a spectacle frame comprising a pair of ophthalmic lenses and/or refractive surgery.

The recommendation may be for at least part of the members of the cohort group to have they view checked, for example based on the monitoring of the behavior it is possible to identify the members that would need to change they ophthalmic prescription.

Such recommendation may be provided directly to the members of the cohort group or sent to an eye care professional that may use the provided recommendation to adjust the recommendation to each members individually.

The vision information may be an alert for at least part of the members of the cohort group.

For example, the vision information may be an alert indicative of the vision state and/or fatigue state and/or none-recommended vision behavior of at least part of the members of the cohort group.

Such alert may be provided directly to the members of the cohort group or sent to an eye care professional that may decide to carry out further vision exam based on such alert.

The vision information may be an activation of at least one functionality on a head mounted device provided to at least part of the members of the cohort group. For example, a filtering functionality may be activated and/or adjusting the optical function of the head mounted device.

The optical function may comprise dioptric function, light transmission, light reflection absorption, polarizing capability, reinforcement of contrast capacity, etc. . . . .

The dioptric function corresponds to the optical lens power (mean power, astigmatism etc. . . . ) as a function of the gaze direction.

The optical function of the head mounted device may comprise the dioptric function of at least one of the lenses that the head mounted device may comprise, a sun protection function for example by controlling a transmission parameter of the head mounted device or the polarization of a surface of at least one of the lenses that the head mounted device may comprise.

For example, the dioptric function may be adapted by adapting the addition in the near zone to relieve the user from the visual fatigue. The color or light absorption of the optical lenses may also be adapted.

The vision information may be an access to a service offer. For example, providing access and/or suggesting access to a specific service that may be useful for the at least part of the members of the cohort group. Typically, the vision information may allow identifying members of the cohort group that would need progressive ophthalmic correction and propose access to an ordering service of progressive ophthalmic lenses.

The vision information may be a comparison information relating to the comparison of the behavior of the members of the cohort group relative to a behavior reference model of the cohort group.

The vision information may be a comparison information relating to the comparison of the behavior of at least one members of the cohort group relative to a behavior reference model of said member of the cohort group.

The vision information may be generated using statistical analysis of the behavior of data over time.

Statistics involves the collection, organization, analysis, interpretation, and/or presentation of measured/collected data. With advances in technology, more extensive and complex computing allows massive amounts of data to be collected, stored and/or processed. Further, methods for evaluating the data are numerous.

Statistical analysis can be employed to process and/or evaluate data received by the visual fatigue module of the invention. The two main types of statistics are descriptive and inferential statistics.

Descriptive statistics includes methods for organizing and summarizing collected data. These methods include, but are not limited to, graphs, tables, charts and measurements such as averages, percentiles, and measures of variation of the data. Data mining for pattern detection, machine learning and artificial intelligence methods, regression modeling and summary statistics can be employed in descriptive statistics.

Inferential statistics is based on methods for making conclusions about data collected based on the evaluation of a sample of the data. For example, predictions can be made regarding the entire set of data. An example prediction can relate to the likelihood that a level of visual fatigue is reached based on the visual behavior data collected. Recommendations can be made according to such predictions.

Statistical methods such as multivariate analyzes, regression analysis can be employed to analyze data. Regression analysis includes techniques for analyzing different variables to determine the relationship between one or more dependent variables and independent variables. For example, the analysis can be employed to determine how the value of a dependent variable changes when a value of one independent variable changes while keeping the values of other independent variables constant. Regression analysis can be employed for prediction and overlaps with the field of machine learning (a branch of artificial intelligence that employs algorithms to identify patterns in data and/or make predictions based on evaluated data).

Different models can be employed in regression analysis to model the relationship between two variables. Linear regression is a type of regression analysis. Linear regression models the relationship between a dependent variable and an independent variable using linear predictor functions. Unknown model parameters are estimated from the data on which multi-linear regression is performed. Interpolation methods can be employed to perform prediction based on values within the set of collected data used for model-fitting while extrapolation can be employed to perform prediction based on values outside the set of collected data.

In linear regression models, the conditional mean of an independent variable given the dependent variable value is typically an affine function. In some cases, the median, or some other quantile of the conditional distribution of the independent variable given the dependent variable is a linear function of the dependent variable.

Non-linear regression is a type of regression analysis in which observed information is modeled by a non-linear function. The non-linear function is a combination of the model parameters and depends on an independent variable.

According to a further embodiment of the invention, the processing of the visual behavior data is done by comparing said visual behavior data with at least one predetermined threshold value.

As represented on FIG. 1, the method according to the invention may further comprise a stimulus exposing step S12. During the stimulus exposing step S12 at least part of the members of the cohort group are exposed to stimulus over a period of time.

In the embodiment illustrated on FIG. 1, at least part of the members of the cohort group are exposed to the stimulus during the behavior monitoring step.

However, at least part of the members of the cohort group could be exposed to the stimulus prior to the behavior monitoring step.

The method of the invention could combine both embodiments, having at least parts of the members of the cohort group exposed to the stimulus prior and during the behavior monitoring step. The same or different members of the cohort group could be exposed to a same or different stimulus during and prior to the behavior monitoring step.

The stimulus may be a visual stimulus. For example, at least part of the members of the cohort group may be exposed to visual stimulus, such as gazing a specific visual target, being exposed to a specific light etc. . . . .

The stimulus may be an auditory stimulus. For example, at least part of the members of the cohort group may be exposed to audio signals, such as sound emitted from a specific part of the environment and/or carrying out a conversation and/or following a speech on a display.

The stimulus environment may also be tactile and/or an olfactory stimulus. For example, at least part of the members of the cohort group may be exposed to tactile from a specific device, such as a smart phone and/or tablet and/or head mounted device.

At least part of the members of the cohort group may be exposed to olfactory signals from a specific device emitting specific compound composition.

The different stimulus may be combined. For example, at least part of the members of the cohort group may be required to gaze at different visual target in a direction corresponding to different audio signals.

The stimulus may correspond to a specific activity. For example, an activity to be carried out by at least part of the members of the cohort group is provided and the behavior of the members of the cohort group is monitored while having the members carry out said activity.

The activity may be for example reading a book, walking, running, going up or down stairs and/or a ladder, rope jumping, watching a movie on a display, using a computer, using a smartphone, driving day and at night, using a tablet.

According to an embodiment of the invention, the method may further comprise a cohort group member profile data providing step S8.

During the cohort group member profile data providing step S8, profile data relating to the profile of each member of the cohort group is provided. The profile of each member comprising at least features relating to the vision of each member, for example the vision prescription of the members and/or a behavior model of each member.

The profile of each member may comprise features relating to the light sensitivity of said member.

The profile of each member may further comprise indication of the type of life of said member, for example urban or rural and/or the ethical sensitivity of said member and/or the size of the eyes of the member, and/or the laterality of the member and/or the ethnicity and/or the gender and/or the age and/or the color of the eyes and/or morphology features and/or current life activity of the member.

As illustrated on FIG. 1, the profile cohort group member profile data providing step S8, is preferably carried out prior to the cohort group behavior monitoring step S10.

The profiles of each members of the cohort group are taken into account when generating the vision information. For example, the prescription of each member is consider before generating an alert and/or a recommendation for such member.

The profile of each member may also be taken into account when selecting the stimulus to which at least part of the cohort group is to be submitted.

As illustrated on FIG. 1, the method may further comprise an environment data providing step S14.

During the environment data providing step S14, the environment data relative to the environment of the cohort group is provided. The environment data may relate to the environment of the cohort group upon monitoring of the behavior. According to such embodiment, the environment data providing step S14 and the cohort group behavior monitoring step S10 are concomitant.

The environment data may further or alternatively relate to the environment of members of the cohort group prior to the cohort group behavior monitoring step S10.

For example, the environment data may relate to the everyday life environment of at least part of the members of the cohort group.

Such environment data may be data measured specifically for each member, for example having each member carry an environment sensor over a specific period of time prior to the cohort group behavior monitoring step S10.

The environment data may also be collected by having at least part of the members of the cohort group answer a set of questions.

The environment data may also be average environment data provided via a lookup table or data base, for example based on the geolocalization of the place of life of the members of the cohort group. For example, based on the region and/or country of life of the members of the cohort group it is possible to determine the average light exposition and/or average light composition and/or the gross domestic product of such region and/or country.

The profile of members of the cohort group may be used to retrieve information concerning their place of life and such information may be used to select in a data base environment information concerning average environment data in their place of life.

The environment data may relate to the light composition and/or exposure and/or spectral composition of natural light and/or the time exposure to artificial light and/or the time spend using a display, such as a smartphone, TV screen, computer screen, and/or the gross domestic product and/or the air composition, for example the quantity of specific chemical compounds.

The environment data may be taken into account when generating the vision information.

According to an embodiment of the invention the cohort group behavior data monitoring step is implemented in a controlled environment, for example a controlled visual environment.

Typically, the cohort group behavior data monitoring step is implemented in environment where the lighting is controlled, for example, the intensity and spectral composition of the lighting is controlled. Such environment data are taken into account when generating the vision information.

According to an embodiment of the invention at least part of the behavior data is measured using behavior monitoring devices. Such behavior monitoring device configured for monitoring the behavior of a cohort group may be provided during a behavior monitoring device providing step S4.

The behavior monitoring device may be mounted devices, such as head mounted device comprising at least a camera configured to monitor the behavior of the member of the cohort group carrying the device and/or of the other members of the cohort group. The behavior monitoring device may comprise a localization sensor, such as a GPS and/or a camera arranged to acquire images of the scene around the member and/or an eye tracking device arranged to monitor the eye behavior of the member carrying the monitoring device.

As illustrated on FIG. 1, the method according to the invention may further comprise an initialization step S6. During the initialization step S6 the behavior monitoring device may initialize based at least on the profile data and/or the environment data of at least part of the members of the cohort group.

The method according to the invention may comprise an optical device providing step S2. Optical devices are provided to at least part of the members of the cohort group during the optical device providing step S2.

For example, the optical devices are ophthalmic devices and/or filtering devices and/or head mounted display devices.

According to such embodiment, it possible to determine and/or compare the performance of optical devices on a cohort group. Indeed, during the vision information generating step the vision information may relate to the performance of the optical devices. The performance of optical devices may be determined by objective measurements of behavior data and/or by having the members answer a set of questions to have a subjective performance information.

As indicated in the description the method of the invention may comprise a segmentation step during which the cohort group is segmented in sub-group of members, for example based on the profile and/or the environment data and/or the behavior data.

For example, the cohort group may be segmented between the members that need an ophthalmic correction and those that do not require any ophthalmic correction.

The cohort group may also be segmented based on the place of life of the members and/or the type of life of the members, for example urban or rural and/or the ethical sensitivity of the members and/or the size of the eyes, and/or the laterality and/or the ethnicity and/or the gender and/or the age and/or the color of the eyes and/or morphology features and/or current life activity of the members. The information on which the segmentation is based may be retrieved from the profile of each member.

Figure 2:
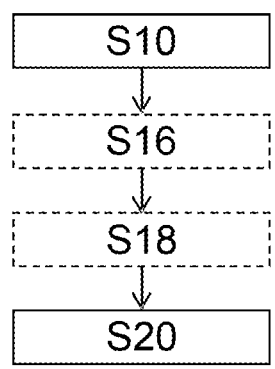
FIG. 2 is an illustration of a chart-flow of a monitoring method according to the invention.

According to an embodiment of the invention illustrated on FIG. 2, the method may further comprise a behavior deviation detection step S16.

During the behavior deviation detection step S16 a behavior deviation of at least one member of the cohort group relative to the behavior of the other members of the group may be detected. For example, at least one member of the cohort group may change his reading distance and have a reading distance very deviating from the other members of the cohort group.

During the behavior deviation detection step S16 a behavior deviation of at least one member of the cohort group relative to the model behavior of the at least one member of the cohort group is detected. For example, the profile of a member of the cohort group comprises a model behavior of such member defining his average reading distance and/or behavior when going up or down the stairs, the method of the invention may comprises determining a deviation relative to such model behavior.

The method according to the invention may further comprise an enhance behavior data monitoring step S18.

During the enhance behavior data monitoring step S18, upon detection of a behavioral deviations in the members of the cohort group, at least one member of the cohort group is identified as a person of interest and is subject to an enhance level of monitoring, for example by monitoring additional features and/or by increasing the monitoring frequency.

For example, if a member has reading distance that deviates relative to the other members and/or to hid model, such member may be identified as person of interest and an enhance level of monitoring may be applied. Typically, more environment data may be measured, additional behavior data may be provided and/or with an increase frequency so as to be able to provide a more accurate vision information.

Advantageously, the method of the invention may be used to compare and/or test a new optical design.

Preferably, the monitoring is carried out over time, for example over a few hours and/or a day in a controlled environment.

Although, the method of the invention has been described as two different embodiments in FIGS. 1 and 2, the method of the invention may comprise any combination of the steps described in FIGS. 1 and 2.

Furthermore, the method according to the invention may comprise the observation of the members of the cohort group by a technical expert so as to determine vision information relating to the vision of the members of the cohort group.

Figure 3:
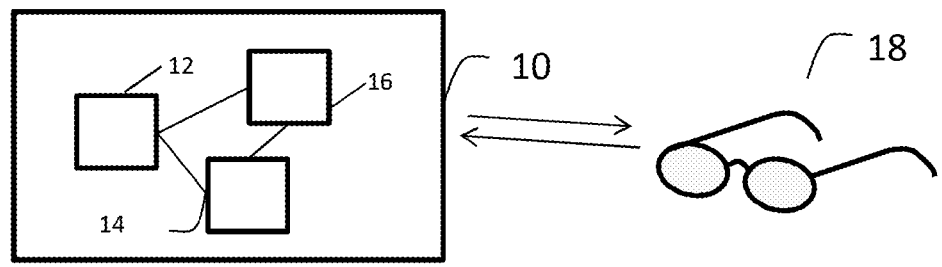
FIG. 3 is a schematic representation of a behavior monitoring device according to the invention.

As illustrated on FIG. 3, the invention also relates to a behavior monitoring device 10 configured for monitoring behavior of a cohort group of members.

The behavior monitoring device comprises:
a communication unit 12,
a memory 14, and
a processor 16.

The communication unit is configured to receive behavior data relating to the behavior of the members of a cohort group of members.

According to an embodiment of the invention, the behavior monitoring device may further comprise at least one sensor configured to sense behavior data and to send said behavior data to the communication unit.

The sensor may be adapted to sense the intensity and/or wavelength and/or direction of electromagnetic radiations, in particular of light radiation in the environment of the cohort group.

Such sensors are typically luminance, photodiode light meter, camera.

The sensor may be an eye tracking device.

The sensor may further comprise temperature and/or humidity sensor to determine the temperature and/or humidity around the cohort group.

The memory 14 stores computer executable instructions and is configured to store the received behavior data.

The computer executable instruction comprises instructions for generating vision information relating to the vision of the members of the cohort group based on the monitoring of the behavior data over time.

The processor 16 is configured for executing the computer executable instructions stored in the memory.

The communication unit may be configured to receive from a distant entity profile and/or stimulus and/or environmental data and the computer executable instructions may comprise instructions for carrying out the steps of the method according to any embodiment of the invention.

As illustrated on FIG. 3, the behavior monitoring device may be arranged to communicate with a head mounted device 18, for example comprising sensors adapted for monitoring the behavior of members of a cohort group. The head mounted device may be smart frames, comprising a frame and at least one sensor, for example a scene camera, an eye tracking device and a GPS sensor.

The behavior monitoring module may be embedded in the head mounted device or may be in a distant entity.

Figure 4:
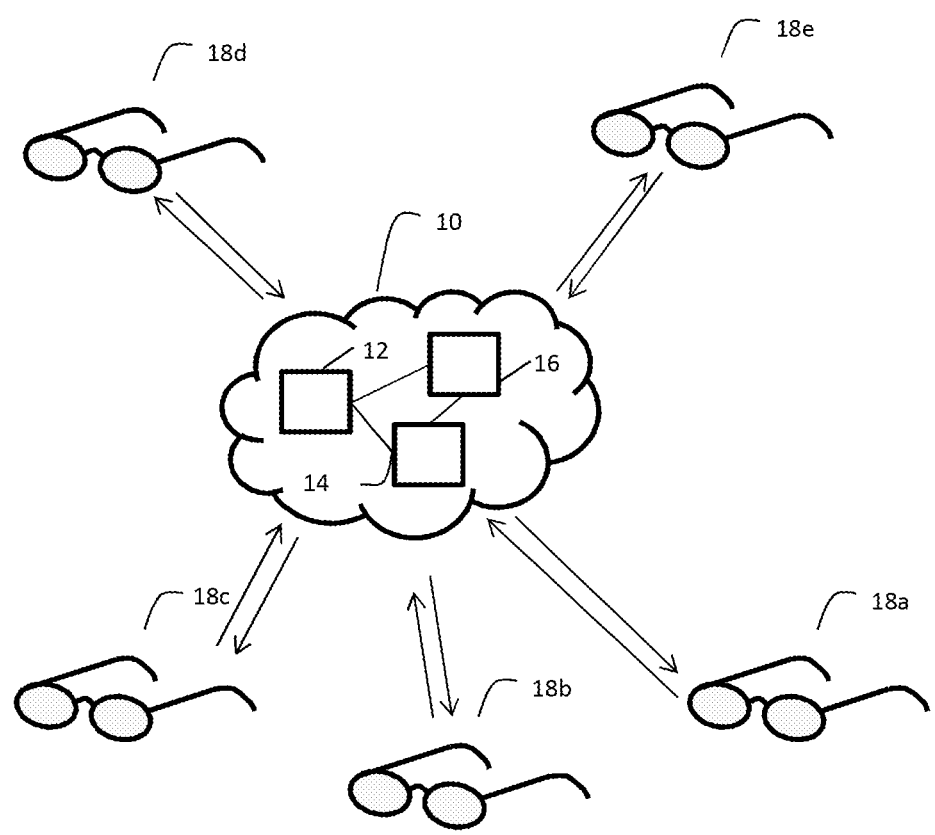
FIG. 4 is a schematic representation of a behavior monitoring system according to the invention.

As illustrated on FIG. 4, the invention further relates to a behavior monitoring system comprising a plurality of behavior sensing devices, for example a plurality of head mounted devices 18a to 18e arranged to sense behavior and/or environment data and to send such data to a behavior monitoring device according to the invention.

Each head mounted device comprises a geolocation module configured to determine geolocation data relative to the geolocation of the member of the cohort group having the head mounted device and the communication component is configured to send geolocation data together with the behavior data and/or environment data a behavior monitoring device.

The behavior monitoring device is arranged to generated vision information based on the behavior data and eventually taking into account the environmental and profile data.

The head mounted devices are arranged to communicate geolocation data and/or data indicative of the behavior of members of the cohort group to each other.

As represented on FIG. 3, all the head mounted devices may be configured to send the data to a single behavior monitoring module. Alternatively, the behavior monitoring system may comprise a plurality of behavior monitoring devices arranged to communicate with a central entity and/or between them.

Each head mounted device can communicate with one or more other head mounted device and/or behavior monitoring device by way of the communications network, either directly or indirectly. The communication is preferably wireless, using Wifi or Bluetooth technologies. Even though illustrated as a single element in FIG. 4, the behavior monitoring system can include other computing devices that provide services to the system and/or can represent multiple interconnected networks, which are not shown.

The network can be the Internet, the computing devices can be Web servers, file servers, media servers, etc. with which the head mounted device and/or environmental analyzing module and/or mapping module communicate via any of a number of known protocols, such as the hypertext transfer protocol (HTTP) or the hypertext transfer protocol secure (HTTPS).

The invention further relates to a controlled environment configured to receive a cohort group of members.

The controlled environment may typically comprise:
means for controlling at least visual environment of the cohort group,
a plurality of sensors configured to measure behavior of the members of the cohort group,
a communication unit configured to send the measured behavior data to a behavior monitoring device according to the invention.

The members of the cohort group may typically be placed in such controlled environment for implementing the method of the invention.

The invention has been described above with the aid of embodiments without limitation of the general inventive concept as defined in the claims.

Many modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method of monitoring a behavior of a cohort group of members, comprising:
an optical device providing step during which optical devices are provided to at least two or more members of the cohort group of members, said two or more members each being provided respectively with an optical device;
a cohort group behavior monitoring step of using a monitoring device to monitor the behavior of members of the cohort group and electronically recording behavior data generated from said monitoring device, the behavior data for each one of the members comprising data of at least one of the group consisting of: gazing direction, gazing distances, eye movements, saccades, accommodation, convergence, relative movement of the head and eyes of the member, and a posture of at least a portion of the body of the member;
an environment data providing step during which environment data relating to a visual environment of the cohort group during the monitoring of the behavior is electronically recorded, the environment data comprising data of at least one of the group consisting of: light composition, light exposure, spectral composition of natural light, time exposure to artificial light, time spent using a display;
a vision information generating step during which vision information relating to the vision of the members of the cohort group is generated and output from the monitoring device based on the behavior data recorded over time,
wherein said environment data are taken into account when generating the vision information, and
wherein said vision information relates to performance of the optical devices.

2. The method according to claim 1, wherein the behavior data is measured data by at least one sensor mounted on the optical devices.

3. The method according to claim 1, further comprising:
a stimulus exposing step during which at least some of the members of the cohort group are exposed to a stimulus over a period of time prior and/or during the cohort group behavior monitoring step.

4. The method according to claim 3, further comprising:
a cohort group member profile data providing step during which profile data relating to a profile of each member of the cohort group is recorded, the profile of each member comprising at least features relating to the vision of each member and/or the behavior of each member, wherein the profile of each member is taken into account during said step of vision information generating.

5. The method according to claim 4, wherein the stimulus is selected based on the profile data.

6. The method according to claim 4, further comprising:
prior to the cohort group behavior monitoring step:
a behavior monitoring device providing step during which a behavior monitoring device configured for monitoring behavior of a cohort group of members is provided,
an initialization step during which the behavior monitoring device is initialized based on the profile data and/or the environment data.

7. The method according to claim 1, wherein the vision information comprises a recommendation, and/or an alert, and/or an activation of at least one functionality on a head mounted device and/or an access to a service offer, and/or a comparison information relating to the comparison of the behavior of the members of the cohort group relative to a behavior reference model of the cohort group, and/or a comparison information relating to the comparison of the behavior of at least one members of the cohort group relative to a behavior reference model of said member of the cohort group.

8. The method according to claim 1, further comprising:
a behavior deviation detection step, during which a behavior deviation of at least one member of the cohort group relative to the behavior of other members of the group and/or relative to a model behavior of the at least one member of the cohort group is detected.

9. The method according to claim 8, further comprising:
an enhanced behavior data monitoring step, during which upon detection of a behavioral deviations in the members of the cohort group, at least one member of the cohort group is identified as a person of interest and is subject to an enhanced level of monitoring.

10. The method according to claim 2, further comprising:
a stimulus exposing step during which at least some of the members of the cohort group are exposed to a stimulus over a period of time prior and/or during the cohort group behavior monitoring step.

11. The method according to claim 2, further comprising:
a cohort group member profile data providing step during which profile data relating to a profile of each member of the cohort group is recorded, the profile of each member comprising at least features relating to the vision of each member and/or the behavior of each member,
wherein the profile of each member is taken into account during said step of vision information generating.

12. The method according to claim 1, wherein the environment data is one of an average light exposition exposed to the group of members and/or an average light composition exposed to the group of members.

13. A behavior monitoring device configured for monitoring behavior of a cohort group of members, the device comprising:
a communication unit;
a memory storing computer executable instructions and configured to store the received behavior data;
a processor for executing the computer executable instructions; and
an optical device,
wherein the computer executable instructions comprise instructions that, upon execution by the processor, causes the communication unit to
receive behavior data relating to the behavior of the members of a cohort group to thereby monitor the behavior and store the received behavior data in the memory, the behavior data comprising data of at least one of the group consisting of: gazing direction, gazing distances, eye movements, saccades, accommodation, convergence, relative movement of the head and eyes of the member, and a posture of at least a portion of the body of the member,
provide environment data relating to a visual environment of the cohort group while monitoring the behavior, the environment data comprising data of at least one of the group consisting of: light composition, light exposure, spectral composition of natural light, time exposure to artificial light, time spent using a display, and
generate and output vision information relating to the vision of the members of the cohort group based on the environment data and the monitoring of the behavior data over time, wherein said vision information relates to performance of the optical device.

14. The behavior monitoring device according to claim 13, further comprising:
at least one sensor configured to sense behavior data and to send said behavior data to the communication unit.

15. A controlled environment configured to receive a cohort group of members, the controlled environment comprising:
the optical device with a diotropic function for controlling a visual environment of the cohort group;
a plurality of sensors configured to measure behavior of the members of the cohort group; and
a communication unit configured to send measured behavior data generated by the plurality of sensors to a behavior monitoring device according to claim 13.

* * * * *